United States Patent
Buckley

(10) Patent No.: US 9,414,944 B2
(45) Date of Patent: Aug. 16, 2016

(54) DEPLOYMENT SLEEVE SHORTENING MECHANISM

(75) Inventor: Kyle R. Buckley, Flagstaff, AZ (US)

(73) Assignee: W. L. GORE & ASSOCIATES, INC., Newark, DE (US)

( * ) Notice: Subject to any disclaimer, the term of this patent is extended or adjusted under 35 U.S.C. 154(b) by 283 days.

(21) Appl. No.: 13/294,092

(22) Filed: Nov. 10, 2011

(65) Prior Publication Data

US 2012/0130474 A1 May 24, 2012

Related U.S. Application Data

(60) Provisional application No. 61/412,621, filed on Nov. 11, 2010.

(51) Int. Cl.
*A61F 2/06* (2013.01)
*A61F 2/97* (2013.01)

(52) U.S. Cl.
CPC .................................. *A61F 2/97* (2013.01)

(58) Field of Classification Search
CPC .......... A61F 2/97; A61F 2/962; A61F 2/966; A61F 2002/9665
USPC ........ 606/108, 191, 194, 200; 623/1.11, 1.12, 623/1.22
See application file for complete search history.

(56) References Cited

U.S. PATENT DOCUMENTS

| | | |
|---|---|---|
| 5,531,717 A | 7/1996 | Roberto et al. |
| 5,676,688 A | 10/1997 | Jaker et al. |
| 5,711,841 A | 1/1998 | Jaker |
| 5,897,535 A | 4/1999 | Feliziani et al. |
| 6,007,488 A | 12/1999 | Jaker et al. |
| 6,206,888 B1 | 3/2001 | Bicek et al. |
| 6,240,968 B1 | 6/2001 | Bigonzi-Jaker et al. |
| 6,322,586 B1 | 11/2001 | Monroe et al. |
| 6,352,561 B1 | 3/2002 | Leopold et al. |
| 7,556,641 B2 | 7/2009 | Cully et al. |
| 7,691,138 B2 | 4/2010 | Stenzel et al. |
| 7,727,163 B2 | 6/2010 | Behl |
| 7,780,716 B2 | 8/2010 | Pappas et al. |
| 2003/0109886 A1 * | 6/2003 | Keegan et al. ............ 606/108 |
| 2003/0233115 A1 * | 12/2003 | Eversull et al. ........... 606/194 |
| 2004/0110442 A1 | 6/2004 | Rhim et al. |
| 2005/0154443 A1 * | 7/2005 | Linder et al. ............. 623/1.11 |
| 2005/0197595 A1 | 9/2005 | Huang et al. |
| 2005/0197627 A1 | 9/2005 | Huang et al. |
| 2006/0009784 A1 | 1/2006 | Behl et al. |
| 2006/0036310 A1 * | 2/2006 | Spencer et al. ........... 623/1.12 |

(Continued)

FOREIGN PATENT DOCUMENTS

| | | |
|---|---|---|
| CA | 2 573 506 | 2/2006 |
| EP | 605427 | 12/1992 |

(Continued)

*Primary Examiner* — Corrine McDermott
*Assistant Examiner* — Sarah Simpson

(57) ABSTRACT

A medical device constraint includes an elastic element having proximal and distal ends, a continuous lumen extending between the proximal and distal ends of the tubular elastic element; and a medical device disposed at least partially within the continuous lumen, wherein the generally tubular element has a first state in which the tubular element is longitudinally held in tension to conceal a gap between the medical device and a distal tip and a second state in which the tubular element is longitudinally relaxed and spaced apart from the gap.

14 Claims, 5 Drawing Sheets

(56) References Cited

U.S. PATENT DOCUMENTS

| | | |
|---|---|---|
| 2006/0074436 A1 | 4/2006 | Behl |
| 2006/0122566 A1 | 6/2006 | Huang et al. |
| 2006/0173525 A1 | 8/2006 | Behl et al. |
| 2006/0178722 A1 | 8/2006 | Jaker et al. |
| 2007/0061605 A1 | 3/2007 | Engler et al. |
| 2007/0106233 A1 | 5/2007 | Huang et al. |
| 2007/0208350 A1* | 9/2007 | Gunderson ............ 606/108 |
| 2007/0233224 A1* | 10/2007 | Leynov et al. ......... 623/1.12 |
| 2007/0276461 A1* | 11/2007 | Andreas et al. ........ 623/1.11 |
| 2010/0249907 A1* | 9/2010 | Dorn et al. ............ 623/1.23 |
| 2010/0262217 A1* | 10/2010 | Bruszewski ........... 623/1.11 |

FOREIGN PATENT DOCUMENTS

| | | |
|---|---|---|
| EP | 696447 | 2/1996 |
| JP | 2000-149537 | 5/2000 |
| JP | 2001-47102 | 2/2001 |
| JP | 2001-85024 | 3/2001 |
| WO | 2005/107644 | 11/2005 |
| WO | 2010/045297 | 4/2010 |
| WO | 2010/063795 | 6/2010 |

\* cited by examiner

DEPLOYMENT SLEEVE SHORTENING MECHANISM

CROSS REFERENCE TO RELATED APPLICATIONS

This application is a non-provisional of, and claims priority to, U.S. Provisional Patent Application No. 61/412,621, entitled "Deployment Sleeve Shortening Mechanism" filed Nov. 11, 2010, the content of which is hereby incorporated by reference in its entirety.

BACKGROUND

1. Field

The present disclosure relates to catheter based systems used to deliver medical devices.

2. Discussion of the Related Art

Various medical devices require catheter based delivery systems. Such medical devices include implantable, diagnostic and therapeutic devices. Common implantable, endovascular devices can include stents, stent grafts, filters, occluders, sensors and other devices. Endovascular devices are commonly advanced through the native vasculature to a treatment site by the use of a flexible catheter. When properly positioned at the treatment site the device (in the case of a stent) can be expanded to appose the vasculature. The device can then be released from the catheter allowing the catheter to be withdrawn from the vasculature. It is desirable to pre-compact endovascular devices into small delivery profiles in order to minimize vascular trauma and enhance maneuverability through torturous anatomies. A highly compacted device is often relatively stiff and is therefore difficult to bend into a small radius. A soft, flexible "olive" or tip is commonly positioned distal to the compacted device at the leading end of the delivery catheter, again to minimize vascular trauma and to enhance the positioning accuracy. As the device is advanced through a curved vessel, the junction between the relatively stiff compacted device and the soft flexible tip can "open up" presenting a gap.

To minimize this gap between a semi-rigid compacted device and a soft flexible leading tip various gap fillers and covers have been suggested. For example, a rigid catheter can be used to constrain a device into a small profile. The rigid catheter can extend distally beyond the device and over a portion of a leading tip, therefore covering a potential gap. The device can be allowed to expand by retracting the rigid catheter.

It remains desirable to have a device delivery system incorporating a releasable sleeve constraint along with an effective means to cover any potential undesirable gap between the compacted device and a leading catheter tip.

DETAILED DESCRIPTION

Figure 1:
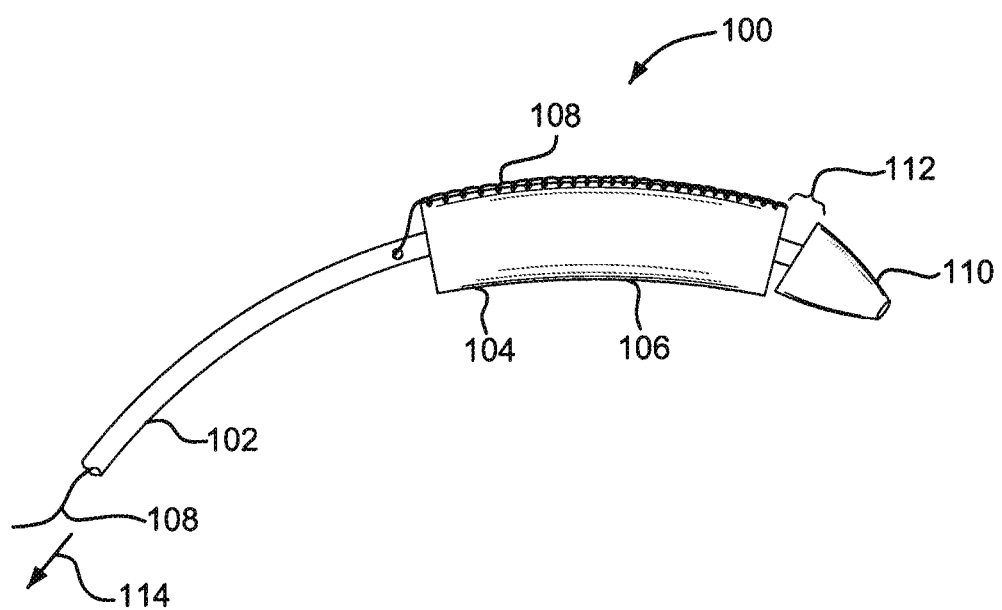
FIG. 1 is a partial side view of a delivery system showing a medical device in a compacted and constrained delivery state and illustrating a gap between the compacted device and a catheter leading tip or olive.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting. Finally, although the present disclosure can be described in connection with various principles and beliefs, the present disclosure should not be bound by theory.

As used herein, the term "elastomer" generally defines a polymer that has the ability to be stretched to at least twice its original length and to retract rapidly to approximately its original length when released. The term "elastomeric" is intended to describe a condition whereby a polymer displays stretch and recovery properties similar to an elastomer, although not necessarily to the same degree of stretch and/or recovery.

In accordance with various embodiments, a partial side view of a catheter system used to implant a medical device is shown and generally indicated at 100 in FIG. 1. The catheter system 100 includes a catheter shaft 102 and an expandable device 104 constrained to a delivery profile or constrained state suitable for endoluminal delivery of the device to a treatment site. The device 104 is held in the constrained state by a flexible, generally tubular constraining sleeve or restraining member 106. The flexible restraining member 106 is held or maintained in a tubular shape by a removable stitch line 108. When the stitch line 108 is actuated by pulling or tensioning in the direction indicated at 114, the restraining member 106 will split open and allow the device 104 to expand. Examples of restraining members and coupling members for releasably maintaining expandable devices in a constrained or collapsed state for endoluminal delivery to a treatment site can be found in U.S. Pat. No. 6,352,561 to Leopold et al, the content of which is incorporated herein by reference in its entirety.

Still referring to FIG. 1, as the catheter system 100 is advanced through a curved vessel, a gap 112 can form between the constrained device 104 and a compliant distal catheter tip 110. Described in greater detail below, the restraining member, in accordance with various embodiments, comprises a retractable section that extends over at least a portion of the compacted or constrained device and at least a portion of the catheter tip so as to cover or bridge a gap therebetween. The retractable section can retract away from the catheter tip sequentially or concurrently with at least a partial actuation or opening of the restraining member.

Figure 2:
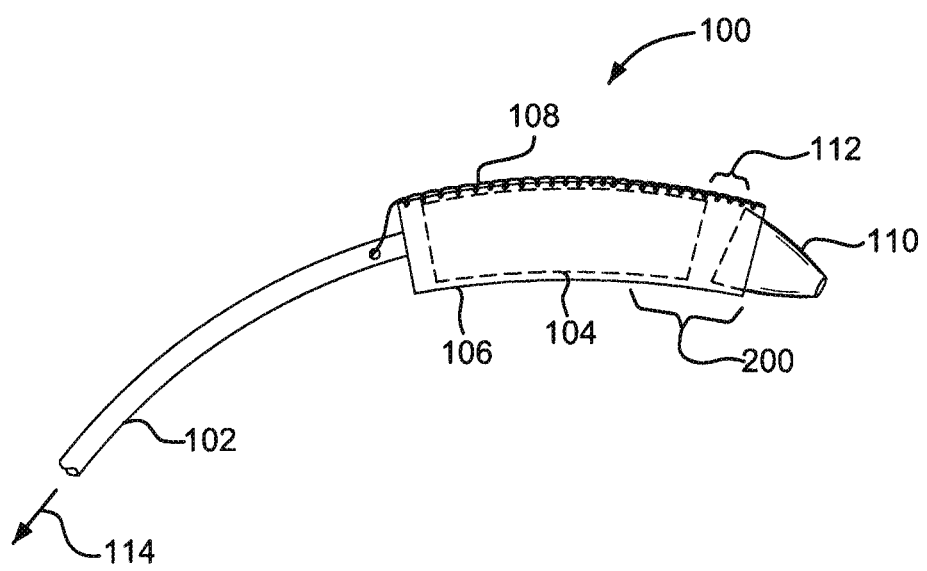
FIG. 2 is a partial side view of a delivery system showing a medical device in a compacted and constrained delivery state, incorporating a restraining member having a retractable section.

Referring to FIG. 2, a partial side view of a catheter system, in accordance with various embodiments, used to implant a medical device is shown and generally indicated at 100. The catheter system 100 includes a catheter shaft 102 having opposite proximal and distal ends, and an expandable device 104 (shown in dashed lines) disposed near or at the distal end of the catheter shaft 102. The device 104 is held in a constrained state suitable for endoluminal delivery of the device to a treatment site by a flexible, generally tubular constraining sleeve or restraining member 106. The flexible restraining member 106 is held in the tubular shape by a removable stitch line 108. When the stitch line 108 is actuated by pulling or tensioning in the direction indicated at 114, the restraining member 106 will split open and allow the device 104 to expand. The restraining member 106 at its distal end incorporates a retractable section 200 that extends over at least a portion of both the device 104 and the catheter tip 110. In various embodiments, the retractable section can be a generally tubular element. As the catheter system is advanced through a curved vessel, a gap 112 can form between the constrained device 104 and a compliant distal catheter tip 110. As shown, the retractable section 200 extends over at least a portion of both the device 104 and the catheter tip 110 to bridge the gap 112 therebetween. The retractable section 200 can retract away from the catheter tip 110 sequentially or concurrently with actuation or opening of the restraining member.

In various embodiments, a retracting element can be operatively coupled to the retractable section to facilitate retraction of the retractable section away from the catheter tip. The retracting element can be an elongated member, such as a tether, wire, string and the like coupled to the retracting section and extending through the catheter for access and selective actuation of the retracting element by the clinician at a proximal end of the catheter.

Figure 2A:
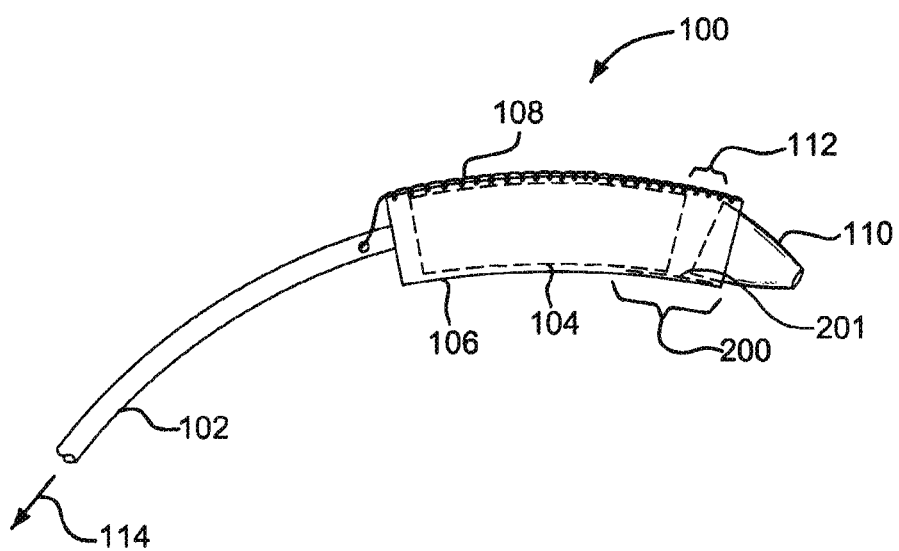
FIG. 2a is a partial side view of a delivery system showing a medical device in a compacted and constrained delivery state, incorporating a restraining member having a retractable section.

In various embodiments, the retracting element, for example as illustrated at 201 in FIG. 2a, can be formed from an elastomeric material and operatively coupled to the retractable section 200, such that the retracting element 201 is in a tensioned state while the retractable section 200 is releasably held or maintained over the device 104 and the catheter tip 110 to bridge the gap 112 therebetween. Release or opening of the retractable section 200 allows the retracting element 201 to shorten as it moves toward a relaxed, untensioned state. The retractable section 200 is pulled or displaced away from the catheter tip 110 in response to the shortening of the retracting element 201.

In various embodiments, the retractable section can be formed from an elastomeric material and tensioned or stretched such that the retractable section can be releasably maintained in a tensioned state while extending over the device and the catheter tip to bridge the gap therebetween, and released to allow movement of the retractable section toward a shortened, relaxed state sequentially or concurrently with opening of the restraining member.

Upon delivery, the restraining member is released allowing the restraining member to release or "split-open" and permit the compacted device to expand. The device can be expanded by a balloon or can expand due to an outward force applied by a compressed stent wire frame. The restraining member may remain with the device at the treatment site in the vasculature, captured between the device and vascular wall. As the restraining member is released, the retractable section of the restraining member retracts proximally away from the catheter tip. In some cases, the medical device has anchors or barbs that aid in securing the device to the vascular wall along with a blood sealing cuff. Thus, retraction of the retractable section can further expose such anchors or barbs and/or sealing cuffs for engaging the vascular wall.

Figure 3A:
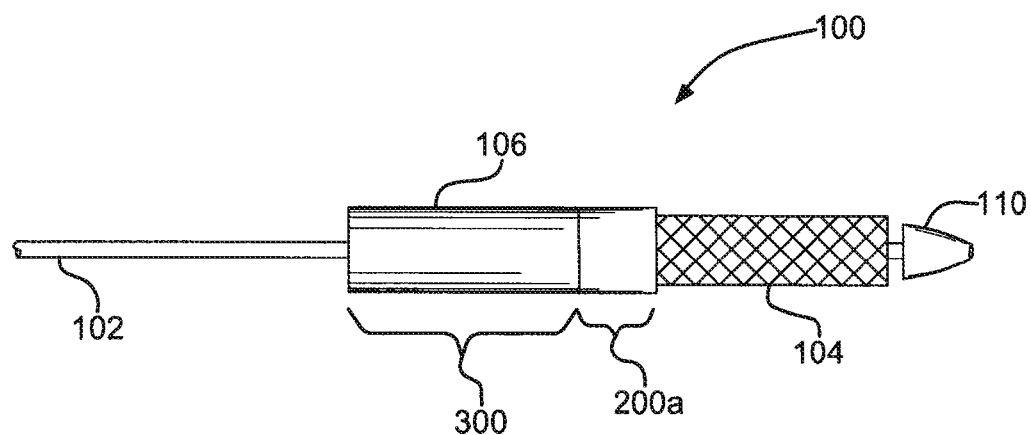
FIGS. 3a and 3b are partial side views of a delivery system showing a medical device in a compacted and constrained delivery state, wherein the device is constrained by a restraining member having a retractable section.
Figure 3B:
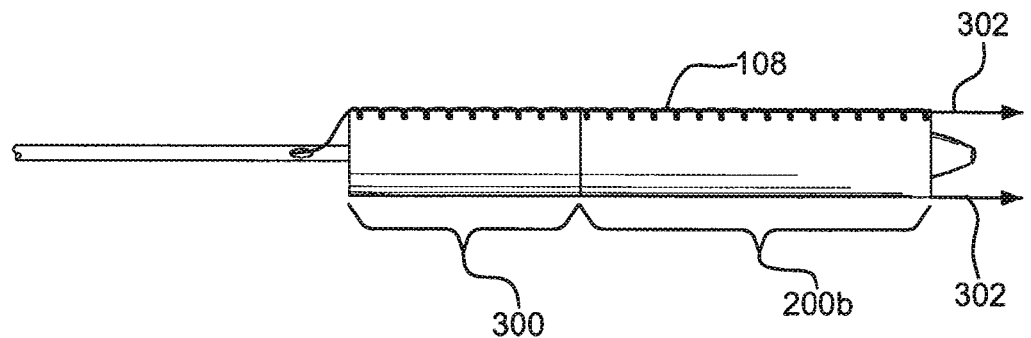

Referring to FIG. 3a, a catheter system 100, in accordance with various embodiments, is shown having an expandable device 104 partially covered by a constraining sleeve or restraining member 106. The restraining member 106 has a retractable section 200a extending from a relatively non-elastic portion 300. The retractable section 200a is shown in a non-tensioned state having a relaxed, original longitudinal length. As shown in FIG. 3b, the retractable section 200b of the restraining member 106 can be longitudinally tensioned (stretched or elongated) in the direction depicted by arrows 302. The retractable section 200b of the restraining member 106 can be stretched longitudinally to extend over the proximal end of the catheter olive or tip 110 to conceal or bridge a gap between the device 104 and the catheter tip 110. Once longitudinally tensioned to the desired stretched length, the retractable section of the restraining member can be longitudinally restrained in tension. The retractable section 200b can, for example, be longitudinally tensioned or stretched to at least about 10% longitudinal elongation or at least about 110% of an initial or original (relaxed) length and held (restrained) in this stretched condition to bridge the gap between the device and the catheter tip. As illustrated in FIG. 3b, a releasable stitch line 108 maintains the retractable section 200b in the elongated, tensioned state.

Figure 3C:
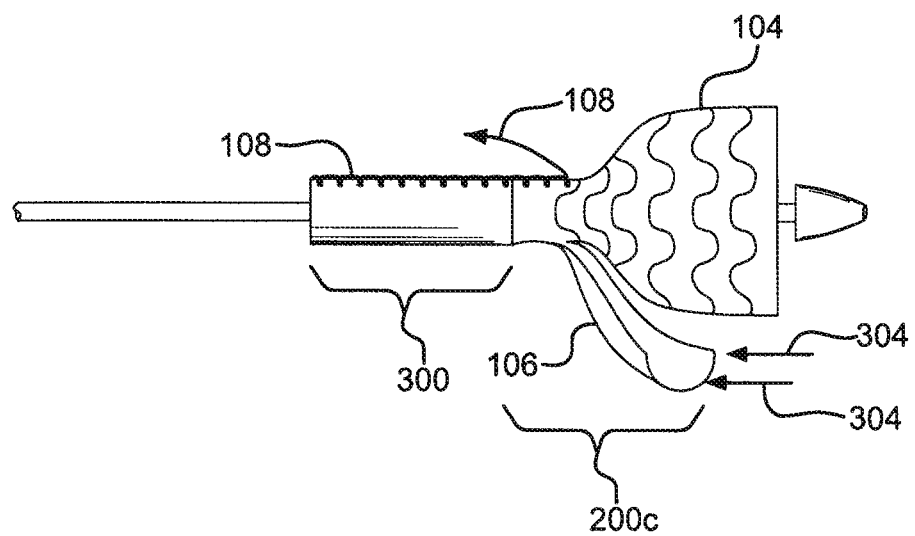
FIGS. 3c and 3d are partial side views of a delivery system showing the release of a constrained medical device

As shown in FIG. 3c, the releasable stitch line 108 can be actuated or tensioned to allow the restraining member 106 to split open and release the expandable device 104. As the restraining member 106 opens, the retractable section 200c is free to retract in the direction depicted by arrows 304 toward a relaxed, non-tensioned state. The restraining member therefore shortens longitudinally in length and retracts proximally along the compacted device. In some cases, the medical device has anchors or barbs that aid in securing the device to the vascular wall along with a blood sealing cuff. By shortening in length, the restraining member can retract proximally to expose any optional anchors and/or sealing cuffs for engaging the vascular wall.

Figure 3D:
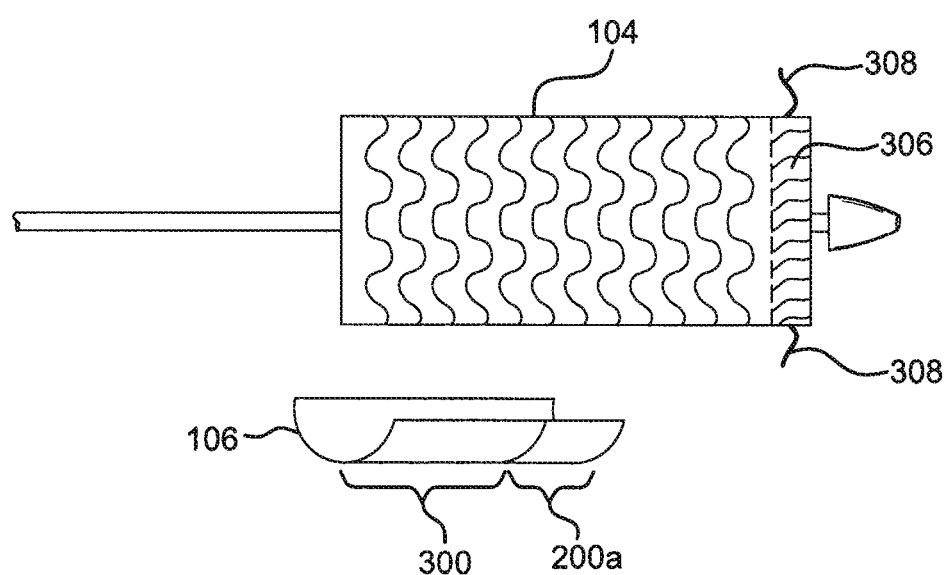

As shown in FIG. 3d, the releasable stitch line can be actuated, allowing the device 104 to fully expand. The retractable section 200a of the restraining member 106 is now longitudinally shortened as it moves toward the relaxed, non-tensioned state, as shown. Since the retractable section 200a is relaxed and non-tensioned, the retractable section retracts to a length shorter than a longitudinally tensioned or stretched length (as illustrated in FIG. 3b, 200b). The restraining member 106 therefore does not cover or interfere with device sealing cuffs 306 or anchor barbs 308, as shown in FIG. 3d.

In various embodiment, a restraining member and retracting element or retractable section of the restraining member can be retained in an elongated and tensioned state by friction between the constrained device and the inner surface of the restraining member. Opening of the restraining member by actuation of the stitch line as described above relieves the friction and allows the restraining member to longitudinally retract as the elastic element returns to a shorter, untensioned state.

In various embodiments, a restraining member can include an elastic element that is held in an elongated tensioned state to conceal a gap along the catheter assembly, such as between the expandable device and an adjacent component of the catheter assembly, and that retracts toward a shortened relaxed state upon release or opening of the restraining member to reveal the gap and/or portions of the expandable device and/or adjacent component.

In various embodiments, the restraining member can include proximal and distal elastic elements which can be held in elongated tensioned states to conceal proximal and distal gaps on opposite ends of the expandable device, and which retract toward shortened relaxed states upon release or opening of the restraining member to reveal the respective proximal and distal gaps and/or portions of the expandable device and/or adjacent components at opposite proximal and distal ends of the expandable device.

Elastic restraining members can comprise a variety of polymeric material, such as silicone. Other exemplary biocompatible elastomers can include, but are not limited to, elastomeric copolymers of 6-caprolactone and glycolide (including polyglycolic acid) with a mole ratio of 6-caprolactone to glycolide of from about 35:65 to about 65:35, more preferably from 35:65 to 45:55; elastomeric copolymers of 6-caprolactone and lactide (including L-lactide, D-lactide, blends thereof, and lactic acid polymers and copolymers) where the mole ratio of 6-caprolactone to lactide is from about 35:65 to about 65:35 and more preferably from about 30:70 to 45:55; other preferable blends include a mole ratio of 6-caprolactone to lactide from about 85:15 to 95:5; elastomeric copolymers of p-dioxanone (1,4-dioxan-2-one) and lactide (including L-lactide, D-lactide, blends thereof, and lactic acid polymers and copolymers) where the mole ratio of p-dioxanone to lactide is from about 40:60 to about 60:40; elastomeric copolymers of 6-caprolactone and p-dioxanone where the mole ratio of 6-caprolactone to p-dioxanone is from about from 30:70 to about 70:30; elastomeric copolymers of p-dioxanone and trimethylene carbonate where the mole ratio of p-dioxanone to trimethylene carbonate is from about 30:70 to about 70:30; elastomeric copolymers of trimethylene carbonate and glycolide (including polyglycolic acid) where the mole ratio of trimethylene carbonate to glycolide is from about 30:70 to about 70:30; elastomeric copolymers of trimethylene carbonate and lactide (including L-lactide, D-lactide, blends thereof, and lactic acid polymers and copolymers) where the mole ratio of trimethylene carbonate to lactide is from about 30:70 to about 70:30; and blends thereof.

Examples of suitable biocompatible elastomers are described in U.S. Pat. Nos. 4,045,418; 4,057,537 and 5,468,253.

An optional external sleeve, or external sock may be incorporated to cover the retractable section of the restraining member.

Typical catheters used to deliver medical devices can comprise commonly known materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenelyne Ether (PPE), Modified Polyphenelyne Ether (Mod PPE), Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluroethylene (ECTFE), Ethylene, Ethylene Tetrafluoroethylene (ETFE), Polychlortrifluoroethylene (PCTFE), Polytetrafluoroethylene (PTFE), Polyvinylidene Fluoride (PVDF), Perfluoroalkoxy (PFA). Other commonly known medical grade materials include elastomeric organosilicon polymers, polyether block amide or thermoplastic copolyether (PEBAX) and metals such as stainless steel and nickel/titanium alloys. Semi-rigid restraining members can comprise appropriate materials listed above.

Medical devices incorporating stents can have various configurations as known in the art and can be fabricated, for example, from cut tubes, wound wires (or ribbons) or flat patterned sheets rolled into a tubular form. Stents can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stents can also comprise bioresorbable materials such as poly(amino acids), poly(anhydrides), poly(caprolactones), poly(lactic/glycolic acid) polymers, poly(hydroxybutyrates) and poly(orthoesters).

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:
1. A catheter assembly comprising:
a catheter having an end;
a catheter tip disposed at the end of the catheter;
an expandable device positioned near the end of the catheter; and
a restraining member extending around at least a portion of the expandable device for releasably maintaining the expandable device in a constrained state suitable for endoluminal delivery of the expandable device,
wherein an end of the expandable device nearest the catheter tip can be spaced apart from the catheter tip to define a gap therebetween,
wherein the restraining member has a retractable section that in a first, longitudinally stretched, state extends over at least a portion of the expandable device and at least a portion of the catheter tip to bridge the gap therebetween and in a second state is axially spaced apart from the catheter tip,
wherein the restraining member further includes a proximal section located proximally relative to the retractable section, the proximal section being relatively less longitudinally stretched than the retractable section when the restraining member is in the first state, and
wherein the proximal section and the retractable section combine to releasably maintain the expandable device in the constrained state.
2. The catheter assembly as set forth in claim 1, wherein the retractable section of the restraining member comprises an elastomeric material, wherein the elastomeric material is axially tensioned in the first state and relieved of said axial tension in the second state.

3. The catheter assembly as set forth in claim 2, wherein the restraining member can be released to allow axial displacement of the retractable section toward a shortened, relaxed state sequentially or concurrently with opening of the restraining member.

4. The catheter assembly as set forth in claim 3, wherein the restraining member is releasably held in the constrained state by a releasable stitch.

5. The catheter assembly as set forth in claim 1, wherein the restraining member is releasably held in the first state by a releasable stitch.

6. The catheter assembly as set forth in claim 1, wherein the restraining member is releasably held in the first state by a releasable stitch.

7. The catheter assembly as set forth in claim 1, further comprising a retracting element operatively coupled to the retractable section to facilitate axial retraction of the retractable section away from the catheter tip,
   wherein the retracting element is an elongated member coupled to the retracting section and extending through the catheter to allow access and selective actuation of the retracting element.

8. The catheter assembly as set forth in claim 7, wherein the retracting element is operatively coupled to the retractable section, such that the retracting element is axially tensioned in the first state and relieved of said axial tension in the second state to cause shortening of the retractable section sequentially or concurrently with opening of the restraining member.

9. The catheter assembly as set forth in claim 1, further comprising a retracting element operatively coupled to the retractable section to facilitate axial retraction of the retractable section away from the catheter tip.

10. The catheter assembly set forth in claim 9, wherein the retracting element is an elongated member coupled to the retracting section and extending through the catheter to allow access and selective actuation of the retracting element.

11. The catheter assembly as set forth in claim 10, wherein the retracting element is operatively coupled to the retractable section, such that the retracting element is axially tensioned in the first state and relieved of said axial tension in the second state to cause shortening of the retractable section sequentially or concurrently with opening of the restraining member.

12. The catheter assembly as set forth in claim 11, wherein the restraining member is releasably held in the first state by a releasable stitch.

13. A medical device constraint assembly comprising:
   an elastic tubular element having proximal and distal ends defining a continuous lumen extending between the tubular element proximal and distal ends,
   wherein the generally tubular element includes a retractable section that provides a first state wherein the retractable section is longitudinally stretched and restrained in tension within the first state, and
   wherein the retractable section further provides a second state wherein the retractable section is longitudinally relaxed,
   wherein the tubular element further includes a proximal section located proximally relative to the retractable section, the proximal section being relatively less longitudinally stretched than the retractable section when the restraining member is in the first state; and
   a medical device having a distal end at least partially contained within the continuous lumen while the tubular element is in the first state,
   wherein the proximal section and the retractable section combine to releasably maintain the medical device,
   wherein the distal end of the medical device is positioned distal to the distal end of the tubular element when the retractable section is in the second state.

14. A catheter assembly comprising:
   a catheter extending between a proximal end and an opposite distal end thereof;
   a catheter tip disposed at the distal end of the catheter;
   an expandable device disposed on the catheter near the distal end;
   a restraining member extending over the expandable device and constraining the expandable device to an outer dimension suitable for endoluminal delivery to a treatment site in a patient; and
   an elastic element fixedly secured to at least two locations on the restraining member to form a retractable section of the restraining member,
   wherein in a first, longitudinally stretched, state, the retractable section extends over a gap between the expandable device and the catheter tip and the elastic element is held in tension due to friction between the expandable device and the restraining member, and in a second state, the restraining member is opened to allow expansion and deployment of the expandable device and further relieve friction to allow longitudinal retraction of the retractable section due to a return of the elastic element to a shorter, untensioned length, and
   wherein the restraining member further includes a proximal section located proximally relative to the retractable section, the proximal section being relatively less longitudinally stretched than the retractable section when the restraining member is in the first state.

* * * * *